United States Patent
Grez et al.

(10) Patent No.: US 9,282,811 B2
(45) Date of Patent: Mar. 15, 2016

(54) INDICATOR SYSTEM FOR REPLACEMENT OF A BRUSH PORTION OF A POWER SKIN BRUSH

(71) Applicant: L'Oréal, Paris (FR)

(72) Inventors: Joseph Grez, North Bend, WA (US); Rachel Stroback, Seattle, WA (US); Scott Straka, Kirkland, WA (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/917,254

(22) Filed: Jun. 13, 2013

(65) Prior Publication Data

US 2014/0366288 A1 Dec. 18, 2014

(51) Int. Cl.
*A46B 15/00* (2006.01)
*A61C 13/02* (2006.01)

(52) U.S. Cl.
CPC ............ *A46B 15/001* (2013.01); *A46B 15/0044* (2013.01); *A46B 15/0085* (2013.01); *A61C 13/02* (2013.01); *A46B 2200/102* (2013.01)

(58) Field of Classification Search
CPC ............. A46B 15/001; A46B 15/0044; A46B 15/0085
USPC .................... 15/22.1, 21.1, 97.1, 28
See application file for complete search history.

(56) References Cited

U.S. PATENT DOCUMENTS

| | | | |
|---|---|---|---|
| 6,314,907 B1 * | 11/2001 | Harris et al. ................... | 116/206 |
| 7,386,906 B2 * | 6/2008 | Roth et al. .......................... | 15/28 |
| 7,786,626 B2 * | 8/2010 | Reishus et al. ................... | 310/36 |
| 8,214,958 B2 * | 7/2012 | Pinyayev et al. ............... | 15/22.1 |
| 8,307,488 B2 * | 11/2012 | Pfenniger et al. .............. | 15/22.1 |
| 8,848,970 B2 * | 9/2014 | Aller et al. .................... | 382/100 |
| 8,938,838 B2 * | 1/2015 | Vashi ............................... | 15/22.1 |
| 2007/0271714 A1 * | 11/2007 | Adam et al. ................... | 15/22.2 |
| 2012/0151697 A1 * | 6/2012 | Farrell et al. ................... | 15/22.1 |

* cited by examiner

*Primary Examiner* — Shay Karls (57) ABSTRACT

The skin brush appliance includes a handle member with a replaceable brushhead assembly. The replaceable brushhead assembly includes a bristle portion which becomes worn in use to the point where it must be replaced to maintain performance of the appliance. An LED light is provided in the vicinity of the bristle portion which is controlled to come on when the bristle assembly is in need of replacement.

16 Claims, 7 Drawing Sheets

INDICATOR SYSTEM FOR REPLACEMENT OF A BRUSH PORTION OF A POWER SKIN BRUSH

TECHNICAL FIELD

This invention relates generally to power skin brushes, and more specifically concerns a system for indicating the appropriate time to replace the brush portion of the skin brush.

BACKGROUND OF THE INVENTION

It is well known that the brush portion of a power skin brush appliance becomes worn after a period of use, to the point where replacement is necessary to maintain performance of the skin brush. However, a user will often continue to use the skin brush without realizing that the brush portion is worn, resulting usually in dissatisfaction with the performance of the skin brush. Different systems and arrangements thus have been developed to help the user recognize when a brush portion needs to be replaced. These include various indications, such as, for instance, a visual or audio use of specific instructions, such as "replace brush".

However, such a language specific approach can be problematic, particularly when the products are sold internationally. Further, while other techniques have used non-language specific icons, those can also be confusing, as there is no established icon for a "replace brush" or similar message.

Accordingly, a system is desired to indicate a worn brush, which needs to be replaced, without using words or specific icons.

DISCLOSURE OF THE INVENTION

Accordingly, such a power skin brush comprises: a handle member; a brushhead assembly portion in a head portion of the handle, mounted so as to be replaceable, where in operation the brushhead assembly includes a bristle portion which becomes worn to the point that its performance is degraded; a light positioned within the skin brush in the vicinity of the brushhead assembly; and a control assembly for indicating operation of the light when the brushhead is worn and due to be replaced, wherein the light is visible to the user.

BEST MODE FOR CARRYING OUT THE INVENTION

Figure 1:
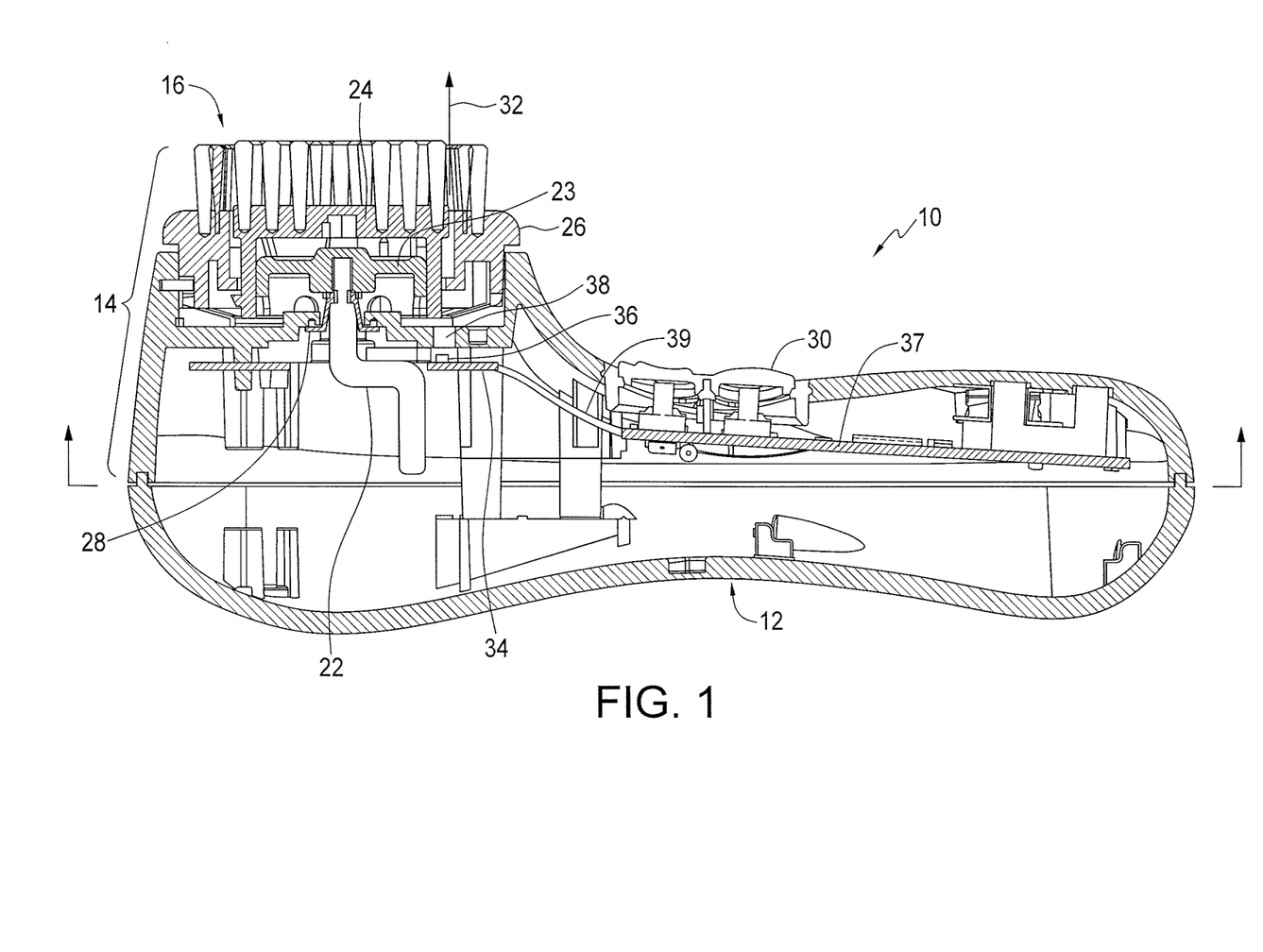
FIG. 1 is a longitudinal cross-sectional view of a power skin brush illustrating the present invention.
Figure 2:
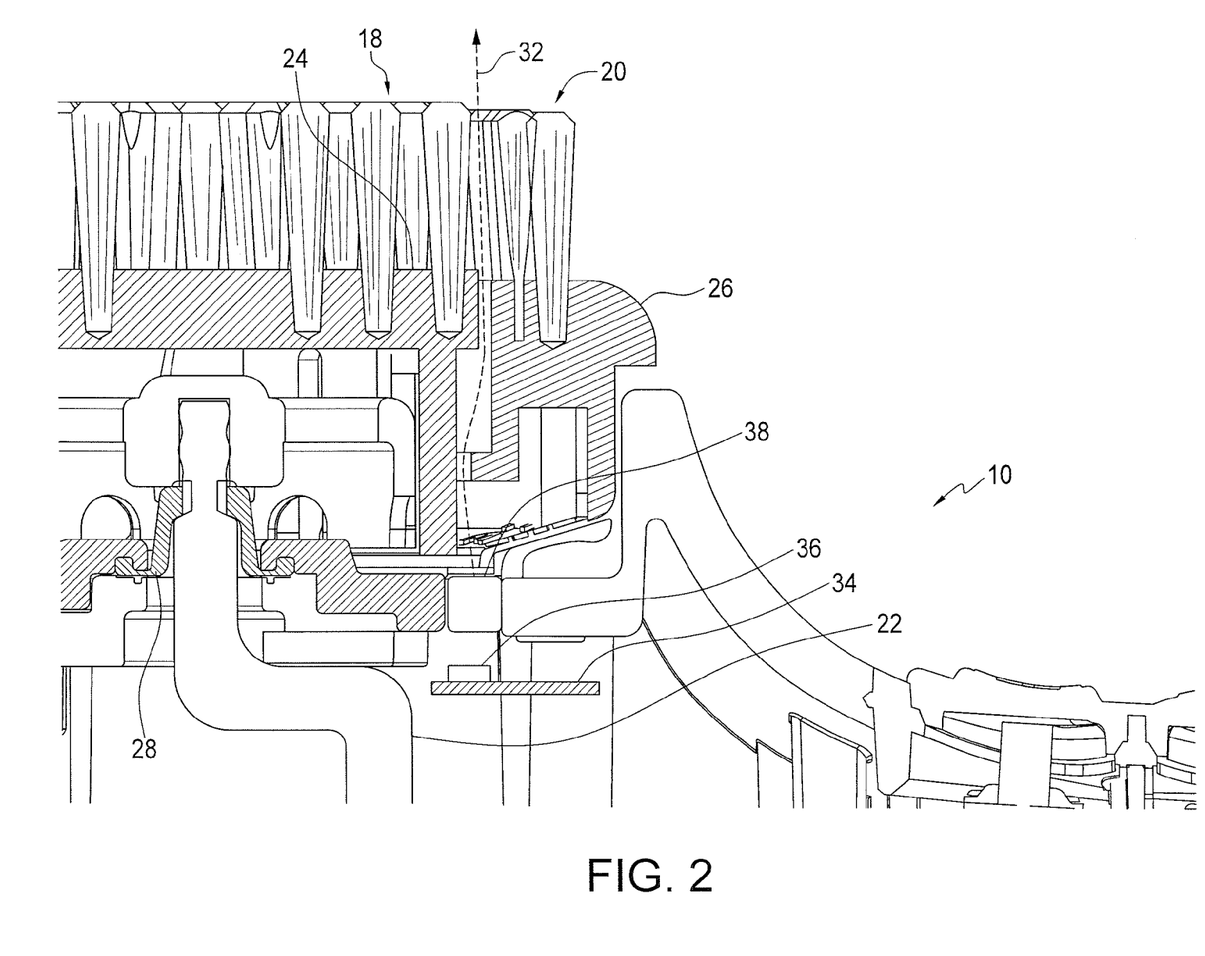
FIG. 2 is an enlarged portion of FIG. 1.
Figure 3:
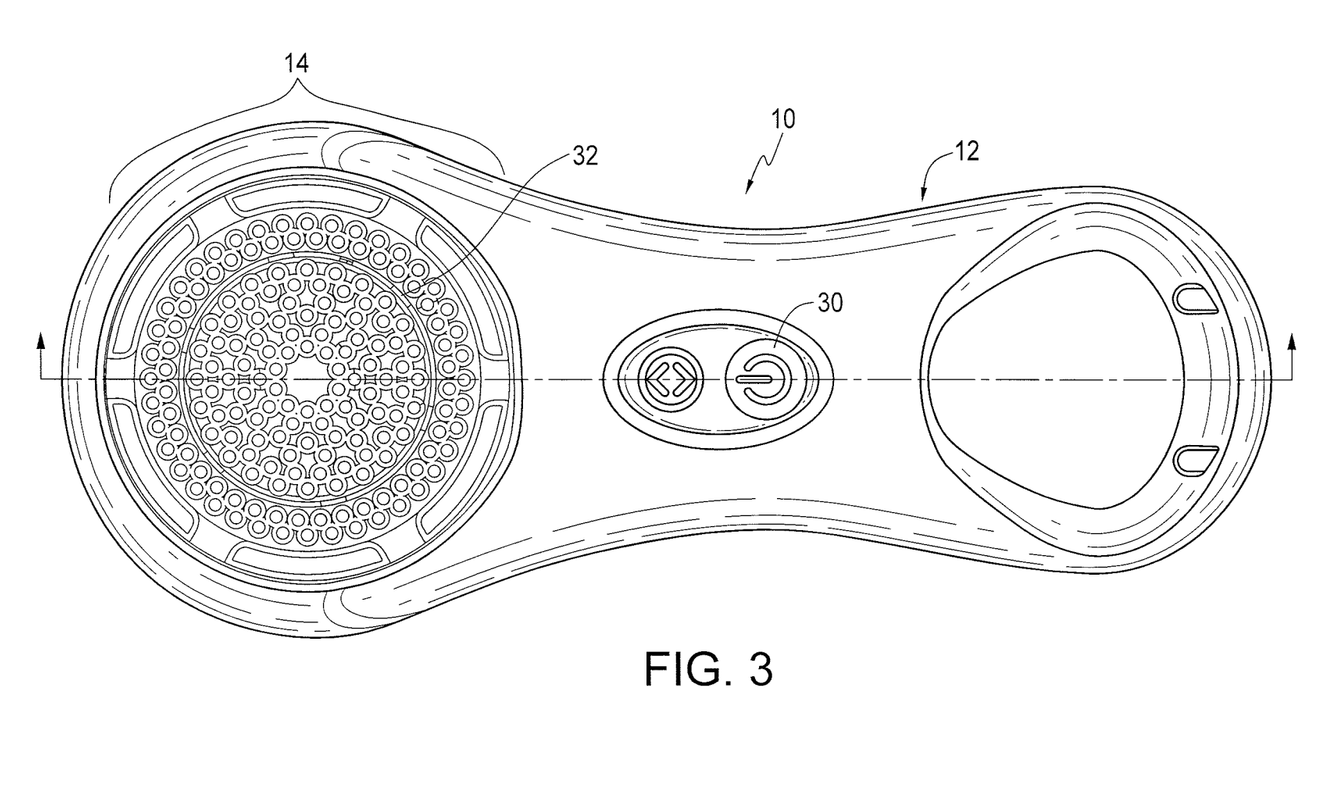
FIG. 3 is a top view of the power skin brush.
Figure 4:
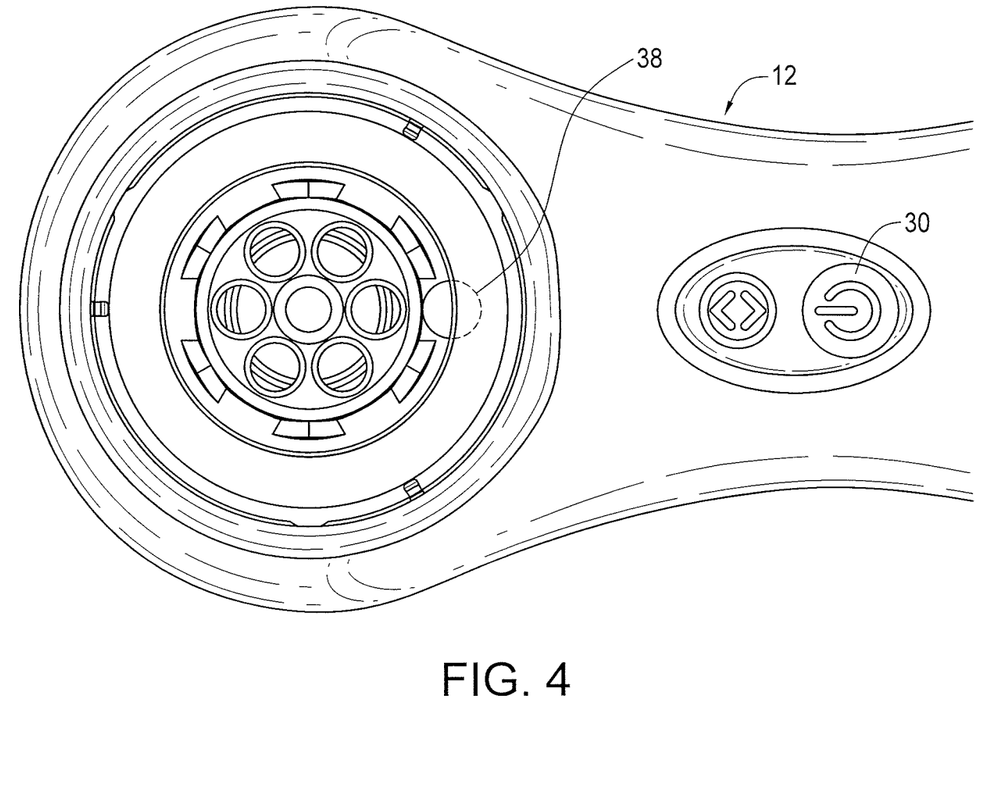
FIG. 4 is a portion of FIG. 3, with the brushhead removed.

FIGS. 1-3 show a power skin brush, generally at 10, which illustrates the general structure of the present invention. The skin brush includes a handle portion 12 with a head end 14 which includes a brush assembly 16. In the embodiment shown, the brush assembly includes an inner bristle portion 18 which includes a plurality of circular rows of bristle tufts, approximately 11 in the embodiment shown, and an outer bristle portion 20 which comprises two rows of bristle tufts surrounding the inner bristle portion 18. Inner bristle portion 18 oscillates back and forth at a predetermined frequency through a predetermined angle, while the outer bristle portion 20 remains fixed. In one embodiment, the frequency is approximately 176 Hz, while the angle of movement is approximately 7°. These values can, of course, be varied.

In the power skin brush of FIGS. 1-3, the inner brush assembly 16 is replaceable, also referred to as a replaceable brushhead. The inner bristle portion of the brushhead is driven by a motor having a drive shaft 22 which engages a hub to which a base 24 is removably attached. The base 24 holds the inner bristle portion. A seal 28 protects the motor against moisture. The motor is controlled by an on/off switch 30. Such brush and motor structures are shown in U.S. Pat. No. 7,786,626 and U.S. Pat. No. 7,386,906, the contents of which are incorporated herein by reference.

In the embodiment shown, there is a space 32 between the moving inner bristle portion and the fixed outer bristle portion, referred to as a light path. A printed circuit board (PCB) 34 is positioned below base 24 of the inner bristle portion, as shown, with an LED 36 mounted thereon. The PCB is also positioned beneath the hub, the handle bulkhead, the seal and the transmission window. An electrical connection 39 is provided from the skin brush microprocessor 37. The LED is mounted such that light from the LED moves first through a translucent window 38 and then through space 32 between base 24 for the inner bristle portion and base 26 for the outer bristle portion, as shown, and then outwardly between the inner and outer bristle portions. The light path should be larger than 0.2 mm. In one embodiment, a plurality of lights are arranged around the periphery of the brush assembly between the inner and outer bristle bases and bristle portions at spaced intervals. One specific example includes six LED lights, although this number can be varied. Even one LED can provide satisfactory results.

The color of the LED can vary. However, since the intention is to bring the need for replacement clearly to the attention of the user, red is a preferred color, although other colors can be used or even multiple colors. In one alternate embodiment, green can be used to indicate that a brush is still in good condition while red can be used to indicate a worn brushhead which needs to be replaced.

The illumination of the lights (LEDs) is controlled by a programmed microprocessor 37 located in the handle. The intensity of the light can also be controlled. It has been discovered that when the light is red, the axial (normal to the printed circuit board) intensity should be more than 20 mcd (milli-candelas), with a 30 level being ideal. With yellow lights, more than 50 mcd should be used, while with white, more than 60 mcd is desirable. Other colors have their own minimal axial intensity levels. The handle typically includes a transmission window for each light which should be at least 2 mm in diameter and comprises material that allows the color of the light being employed to be transmitted with an axial intensity of at least 30 mcd.

While in one embodiment the presence of light (e.g. red) indicates the need for immediate brushhead replacement, light can also be used to provide an advance indication of replacement, with some amount of further use of the brushhead at a good performance level still being available.

Figure 5:
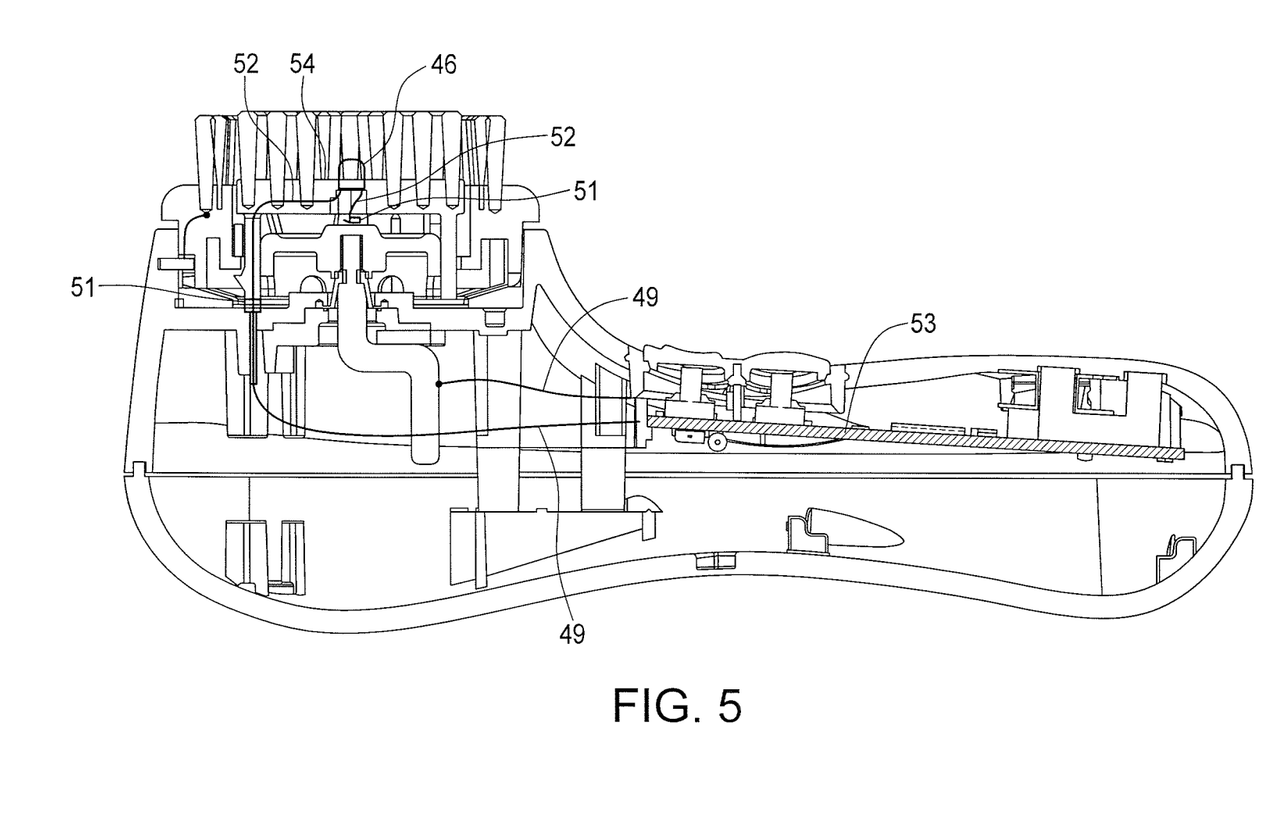
FIG. 5 is a cross-sectional view of a skin brush with an alternate LED placement.

While it is preferred that the lights be positioned between the inner and outer bristle portions, as shown in FIG. 1, other light positions can be used. In one case, as shown in FIG. 5, an LED 46 can be positioned in the head end of the appliance itself. This will require electrical wire or leads 49, electrical connections 51 and conductive leads 52 on or in the brushhead 54 from the microprocessor 53 to the head or a separate battery in the head with an electric or electromagnetic control signal indicating the end of brushhead useful life.

In another alternative, the transmission window can be eliminated, with the LED mounted in the handle material in the same position as the window. The LED encapsulation can be used as a window.

Figure 6:
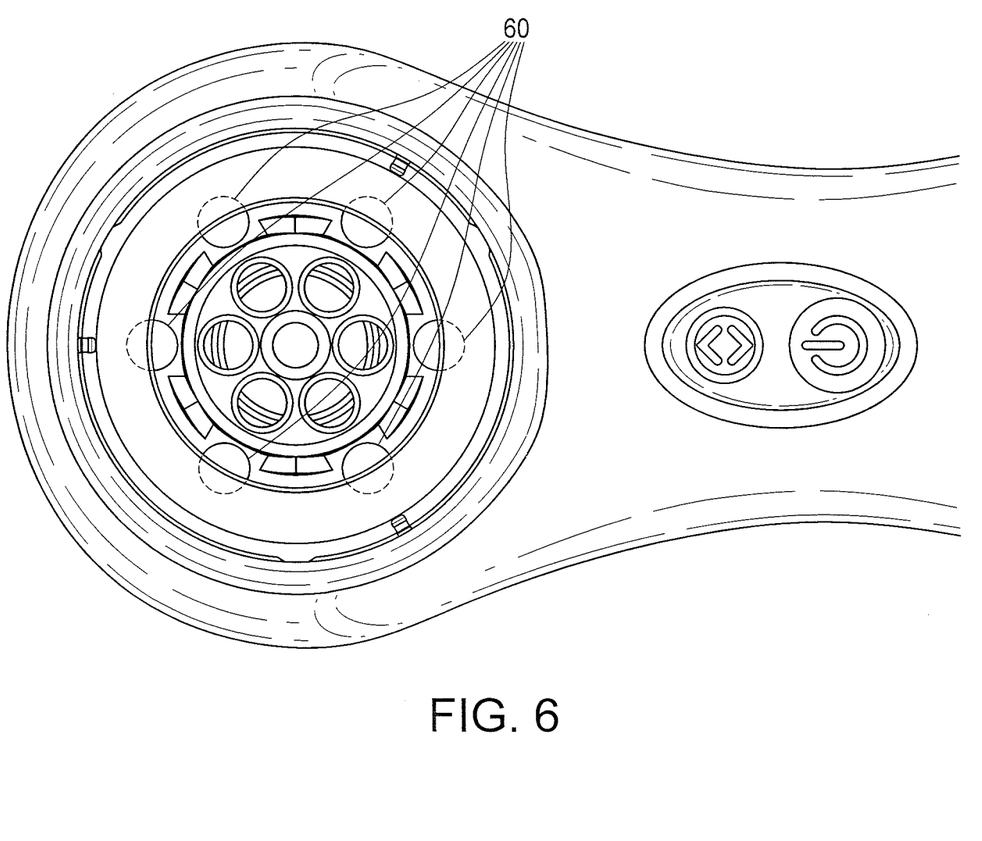
FIG. 6 is a top view of a skin brush with components removed for clarity showing a multiple LED arrangement.

In still another alternative, shown in FIG. 6, a plurality of transmission windows or LEDs 60 can be provided around the periphery of the outer or fixed section of bristles, while still another alternative is to provide the head section with a clear or translucent plastic material which would allow different LED placement arrangements.

The LEDs can be controlled to produce a flashing effect. The preferred flashing routine is likely to be a flash at 1.0 second intervals, with a 50% on time. In an alternative, a slow or gentle start and/or end for each flash event is provided, i.e. a fade-in and/or fade-out of the light for each flash. In one such embodiment, the light is off for 0.25 second, then light is initiated and increases to full power (intensity) in 0.25 second, remaining at full for 0.25 second. The light then fades to off in 0.25 second, after which the loop (sequence) begins again.

Other preferred flashing rates can vary between 0.20 second up to 10 seconds. The on time of light can also vary between 0.20 second to 10 seconds. A non-flashing light can also be used in one embodiment, which fades away at a particular rate. One example of such an arrangement would be an on time between 1.0 second and up to 10 minutes, with a fade between 0.25 to 20 seconds. In one particularly preferred condition, the light is on for 10 seconds and then fades over 10 seconds.

The light can be controlled relative to the use of the appliance. In one embodiment, the light comes on when the appliance is turned on and again when the appliance is turned off for a specific time and manner, as discussed above. However, other on/off times/events can be used, such as upon inserting or removing the appliance from a charger.

As an additional feature, text can be included with the handle such as on the rear of the head part, to the effect that when the light is on, a message to replace the brushhead is illuminated. Also, the message can be placed on the drive hub of the brush assembly, such that when the brushhead is removed from the handle, the user is reminded that replacement is indicated by the presence of the light, which prompts them to replace the brushhead.

Figure 7:
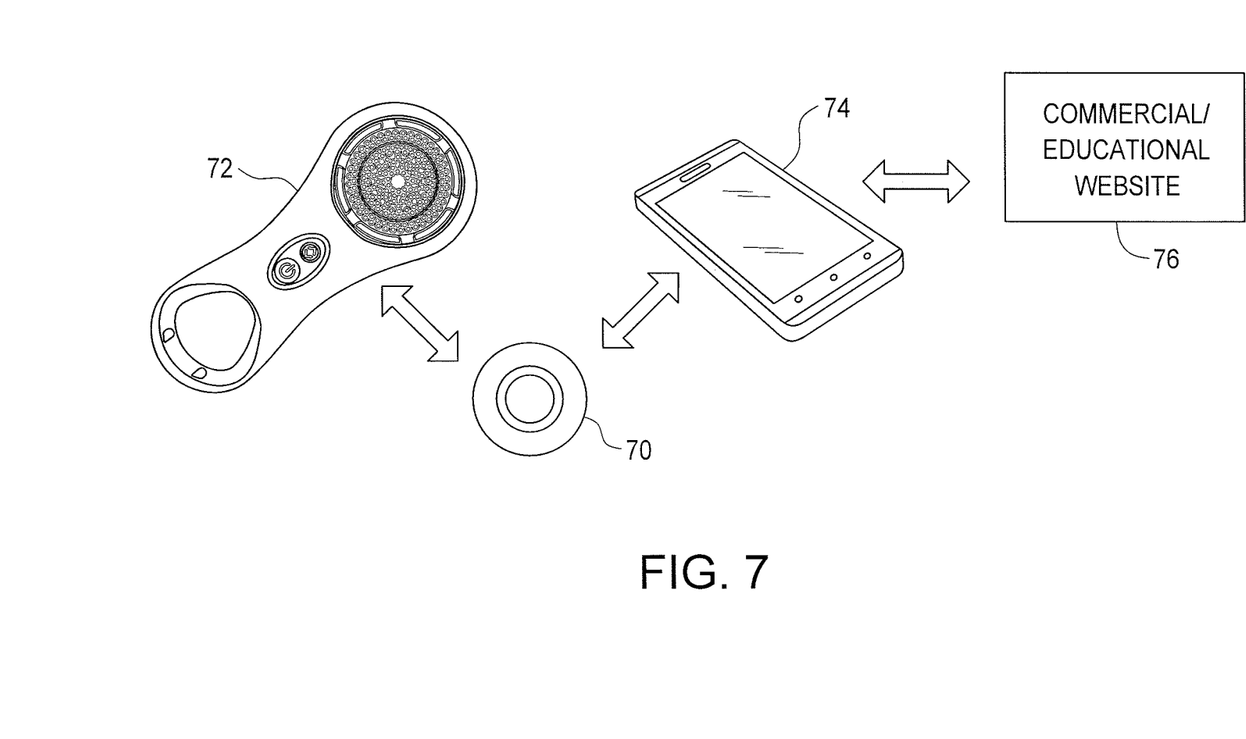
FIG. 7 is a diagram showing the use of the system of FIG. 1 in an ecommerce application.

Referring now to FIG. 7, RFID tagged brushes 70 for a skin care appliance 82 are readable by mobile devices 74, such as smartphones and tablets, among other devices equipped with embedded RFID readers, to enable ecommerce activity, such as communication with a commercial website 76. The RFID tag on the replaceable brushhead, upon being read by the mobile device, directs the device to a particular website through its URL. The website 76 will include various information, including purchase of replacement brushheads, new skin treatment formulations which are specific to specific brushes and even customer-specific formulation/brush combinations. Specialized and newly developed skin treatment protocols may be viewed and/or purchased from the website as well, with the purchase of protocols being directly downloadable to the user's mobile device 74 and from there loaded onto the RFID tag on the brushhead in the appliance 72 to provide additional functionality for the appliance.

Further, available tracking information/capability may be used to identify specific users of the appliance, so that targeted promotional offers can be directed to the user's specific mobile device. The website can also enhance timely brush replacement by providing reminders/notifications to the user's smartphone, mobile devices or other similar device.

Further, the camera capability of a typical mobile device may be used to record areas of a user's face for transmittal to a website accessible by skin treatment professions and/or clinicians for assessment and recommendation of specific brush formulations, or even a virtual web chat, in which a remote clinician can assess the users' photos and provide direct recommendations.

The RFID tag on a brushhead can also be used to direct the mobile device user to an educational website which provides educational information, including newly available brushes, formulations, cleansing protocols and cosmetic techniques for the particular brush or appliance combination.

An appliance itself (the handle portion, for instance) can be used to scan both an RFID tagged brush, and an RFID tagged formulation. This appliance may then unlock new cleansing protocols present in the RFID tags or the handle which are specifically relevant to or coordinated with the brush/formulation previously scanned. One example of such a system would be a pedicure device which scans both a pedi scrub formulation and a pedi brush member and which then operates at a predefined specific frequency, power level and operational profile available in the RFID tags on the appliance to deliver optimal effects relative to a specific formulation.

The appliance itself can also be used to scan cosmetic formulations with an RFID tag having a temporary authorization code, which enables the appliance to operate a specific cleansing protocol for a fixed or limited amount of time. Such a system could be used to provide a trial use of the new formulation/protocol combination, thereafter requiring purchase of a quantity of the formulation to permanently unlock the protocol in the appliance.

Although a preferred embodiment of the invention has been disclosed for purposes of illustration, it should be understood that various changes, modifications and substitutions may be incorporated in the embodiment without departing from the spirit of the invention, which is defined by the claims which follow.

What is claimed is:

1. A power skin brush, comprising:
   a handle member;
   a brushhead assembly portion in a head portion of the handle, mounted so as to be replaceable, where in operation the brushhead assembly includes a bristle portion comprising a plurality of circular rows of bristle tufts which becomes worn to the point that its performance is degraded;
   a light positioned within the skin brush in the vicinity of the brushhead assembly; and
   a control assembly for initiating illumination of the light only when the brushhead is worn and due to be replaced, wherein the light is visible to the user.

2. The appliance of claim 1, wherein the light is an LED light.

3. The appliance of claim 1, wherein the light is red in color.

4. The appliance of claim 1, wherein replacement of the brushhead assembly is determined by the number of times of use of the appliance.

5. The appliance of claim 1, wherein replacement of the brushhead assembly is determined by the length of time the brushhead is in use.

6. The appliance of claim 1, wherein the brushhead assembly includes an inner removable portion with an inner brush base and an outer fixed portion with an outer brush base, and wherein the light is positioned beneath the brushhead assembly so as to shine through a space between the inner and outer brush bases.

7. The appliance of claim 1, including a plurality of lights.

8. The appliance of claim 7, wherein the lights are evenly spaced.

9. The appliance of claim 7, wherein the lights are positioned within a head portion of handle, apart from the brushhead assembly.

10. The appliance of claim 7, wherein the light or lights are LED lights, the appliance including a translucent window associated with each LED light.

11. The appliance of claim 2, wherein a head portion of the handle is translucent and the LED light or lights are positioned at selected positions within the housing.

12. The appliance of claim 1, wherein the light is controlled to produce a flashing of the light.

13. The appliance of claim 12, wherein the flashing occurs every second, with an approximately 50% on time.

14. The appliance of claim 12, wherein the flashing includes fade-in and fade-out times with an intermediate full on time.

15. The appliance of claim 1, wherein the light is turned on when the appliance is turned on, turned off or both.

16. The appliance of claim 1, wherein the light is turned on when the appliance is positioned in or removed from an associated charger base.

* * * * *